(12) United States Patent
Sorensen et al.

(10) Patent No.: US 11,224,740 B2
(45) Date of Patent: Jan. 18, 2022

(54) METHOD AND APPARATUS FOR TEMPORARILY ANCHORING SENSORY NERVE STIMULATOR (SNS) LEADS TO THE SKIN OF A PATIENT DURING SNS TRIALING AND/OR FOR TEMPORARILY ANCHORING OTHER ELONGATED FLEXIBLE ELEMENTS TO THE SKIN OF A PATIENT

(71) Applicant: Anchor Innovation Medical, Inc., Basking Ridge, NJ (US)

(72) Inventors: Peter Sorensen, Basking Ridge, NJ (US); Daniel Morgan, Basking Ridge, NJ (US); Christopher Runnells, Basking Ridge, NJ (US)

(73) Assignee: Anchor Innovation Medical, Inc., Basking Ridge, NJ (US)

( * ) Notice: Subject to any disclaimer, the term of this patent is extended or adjusted under 35 U.S.C. 154(b) by 214 days.

(21) Appl. No.: 15/801,898

(22) Filed: Nov. 2, 2017

(65) Prior Publication Data

US 2018/0117301 A1    May 3, 2018

Related U.S. Application Data

(60) Provisional application No. 62/428,186, filed on Nov. 30, 2016, provisional application No. 62/416,527, filed on Nov. 2, 2016.

(51) Int. Cl.
| | |
|---|---|
| *A61N 1/04* | (2006.01) |
| *A61N 1/372* | (2006.01) |
| *A61N 1/36* | (2006.01) |
| *A61N 1/05* | (2006.01) |

(52) U.S. Cl.
CPC ......... *A61N 1/0492* (2013.01); *A61N 1/0456* (2013.01); *A61N 1/36017* (2013.01); *A61N 1/372* (2013.01); *A61N 1/0551* (2013.01); *A61N 1/36062* (2017.08)

(58) Field of Classification Search
CPC . A61N 1/0492; A61N 1/0456; A61N 1/36062
See application file for complete search history.

(56) References Cited

U.S. PATENT DOCUMENTS

| | | | |
|---|---|---|---|
| 4,029,103 | A | 6/1977 | McConnell |
| 5,147,320 | A | 9/1992 | Reynolds et al. |
| 6,387,076 | B1 | 5/2002 | Landuyt |
| 6,582,403 | B1 | 6/2003 | Bierman et al. |
| 2005/0182368 | A1 | 8/2005 | Gillis et al. |
| 2012/0216385 | A1 | 8/2012 | Taylor |
| 2014/0148778 | A1 | 5/2014 | Levy |

(Continued)

FOREIGN PATENT DOCUMENTS

WO    WO 2017/184857    10/2017

OTHER PUBLICATIONS

Boston Scientific, Fixate[TM] Suturing Device Directions for Use, 2013.

(Continued)

*Primary Examiner* — Joseph M Dietrich
(74) *Attorney, Agent, or Firm* — Pandiscio & Pandiscio

(57) ABSTRACT

A novel method and apparatus for securing an object to a patient. In one form of the invention, the object comprises a sensory nerve stimulator (SNS) lead. And in one form of the invention, the object is secured to a patient using a capstan effect.

21 Claims, 17 Drawing Sheets

(56) References Cited

U.S. PATENT DOCUMENTS

2015/0051621 A1   2/2015  Sorensen et al.
2015/0133891 A1   5/2015  Rosenhan
2015/0246207 A1   9/2015  Khalaj

OTHER PUBLICATIONS

Boston Scientific, Percutanous Leads: Directions for Use, 2017.
StayFIX[R] Fixation Device Instructions for Use, Merit Medical Systems, Inc.

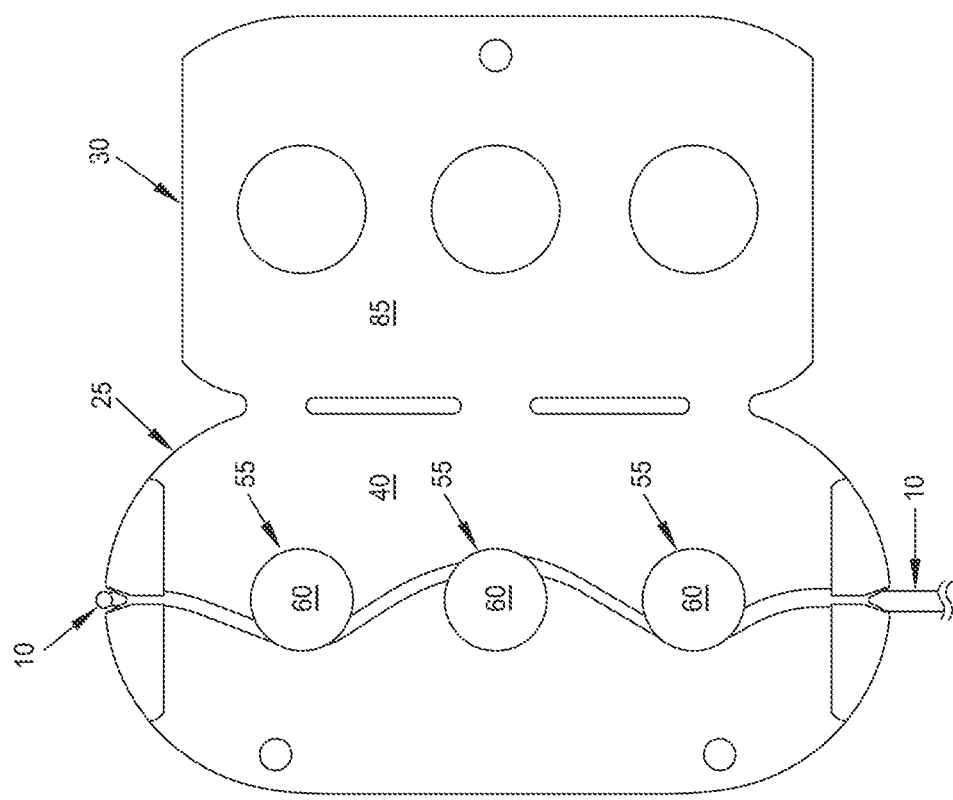

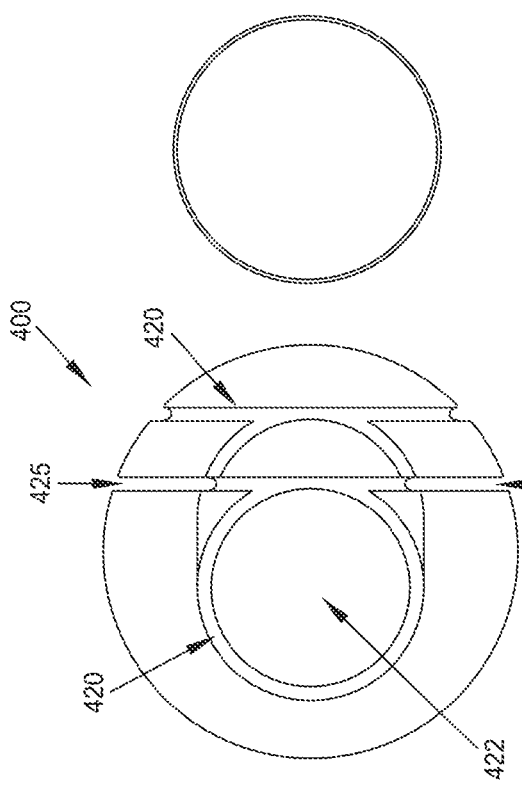
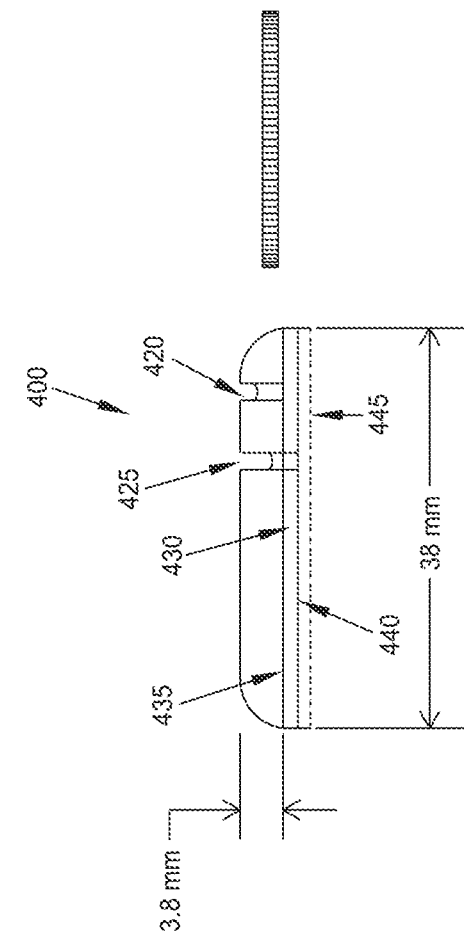

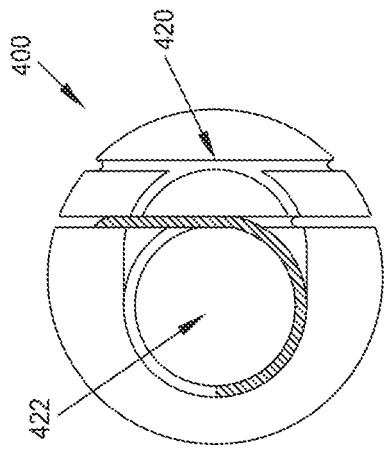
FIG. 20
Peel away paper backing to expose adhesive backing & slide lead into slot and stick to skin.
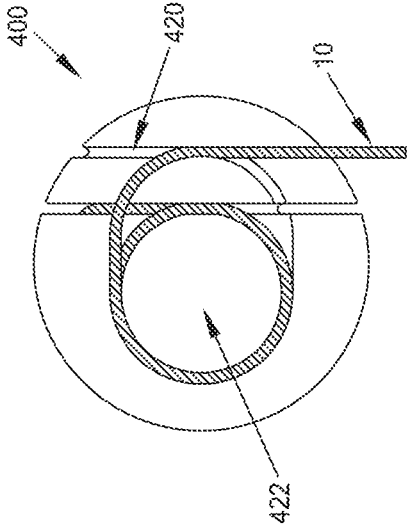
FIG. 21
Wrap the exposed lead around the Central circle and press into groove.
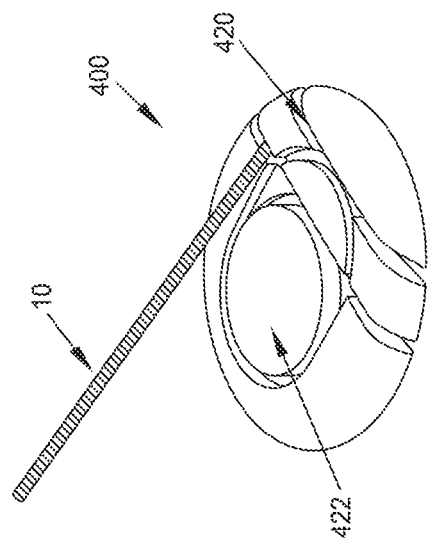
FIG. 22
Wrap the exposed lead around the Central circle a second time.
FIG. 23
Cross over the lead and exit off the disk in the outer groove & remove all slack.

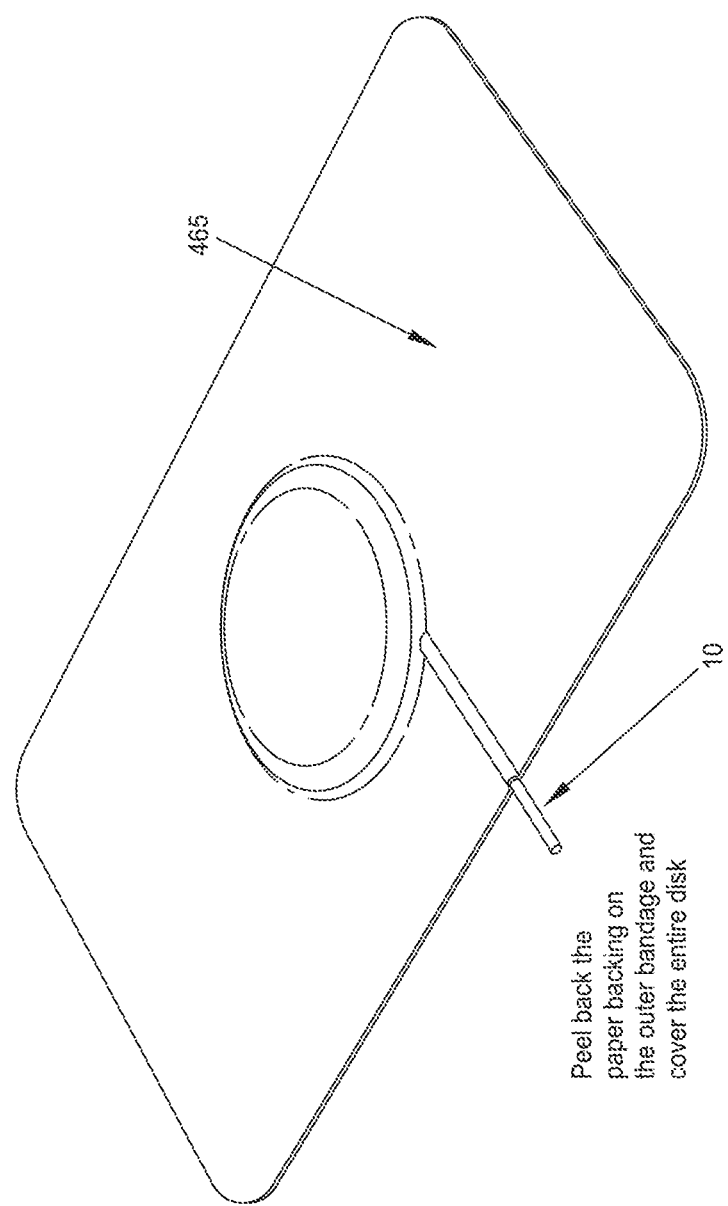

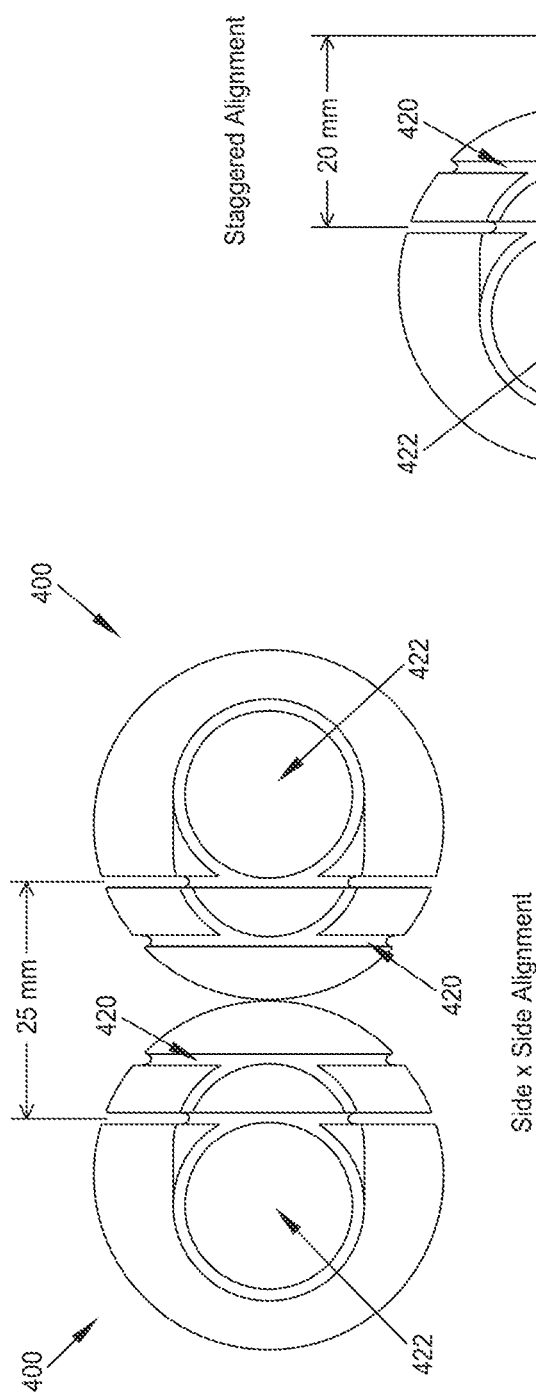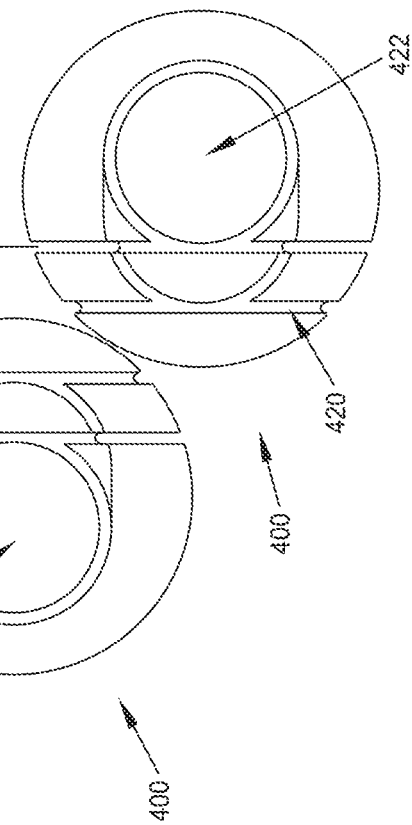

METHOD AND APPARATUS FOR TEMPORARILY ANCHORING SENSORY NERVE STIMULATOR (SNS) LEADS TO THE SKIN OF A PATIENT DURING SNS TRIALING AND/OR FOR TEMPORARILY ANCHORING OTHER ELONGATED FLEXIBLE ELEMENTS TO THE SKIN OF A PATIENT

REFERENCE TO PENDING PRIOR PATENT APPLICATIONS

This patent application claims benefit of:
(i) prior U.S. Provisional Patent Application Ser. No. 62/416,527, filed Nov. 2, 2016 by Suture Concepts Inc. and Peter Sorensen et al. for METHOD AND APPARATUS FOR TEMPORARILY ANCHORING SENSORY NERVE STIMULATOR (SNS) LEADS TO THE SKIN OF A PATIENT DURING SNS TRIALING; and
(ii) prior U.S. Provisional Patent Application Ser. No. 62/428,186, filed Nov. 30, 2016 by Suture Concepts Inc. and Peter Sorensen et al. for METHOD AND APPARATUS FOR TEMPORARILY ANCHORING SENSORY NERVE STIMULATOR (SNS) LEADS TO THE SKIN OF A PATIENT DURING SNS TRIALING.

The two (2) above-identified patent applications are hereby incorporated herein by reference.

FIELD OF THE INVENTION

This invention relates to sensory nerve stimulators (SNS) in general, and more particularly to methods and apparatus for temporarily anchoring sensory nerve stimulator (SNS) leads to the skin of a patient during SNS trialing. This invention also relates to other elongated flexible elements, and for temporarily anchoring such other elongated flexible elements to the skin of a patient.

BACKGROUND OF THE INVENTION

In sensory nerve stimulation therapy (sometimes also referred to as "neuro modulation"), electrical leads are positioned adjacent to selected nerves of a patient and used to deliver electrical stimulation to those nerves so as to provide pain relief to the patient.

In one significant application of sensory nerve stimulation therapy, sensory nerve stimulator (SNS) leads are disposed adjacent to nerves in the spinal column of a patient, whereby to deliver electrical stimulation to those nerves and thereby provide pain relief to the patient. See, for example, FIGS. 1 and 2, which show an SNS system 5 disposed adjacent to the spinal column of a patient. SNS system 5 generally comprises SNS leads 10 and an SNS electrical pulse generator 15. In use, SNS leads 10 are disposed in the spinal column of a patient so that the distal ends of the SNS leads (i.e., the ends of the leads containing the electrodes) lie adjacent to the nerves which are to be treated, and SNS electrical pulse generator 15 applies appropriate electrical pulses to the SNS leads so as to provide sensory nerve stimulation therapy to the patient.

In practice, it is common to conduct a "trial" of the SNS system so as to verify proper electrode placement and appropriate analgesic efficacy for the patient. After proper electrode placement and appropriate analgesic efficacy have been verified by trialing, the SNS system is thereafter permanently installed in the patient.

More particularly, during such "trialing", the distal ends of the SNS leads (i.e., the ends of the leads containing the electrodes) are positioned adjacent to appropriate nerves in the spinal column of the patient, and the proximal ends of those SNS leads are brought out through the skin of the patient for connection to an SNS electrical pulse generator. During the trialing, the proximal ends of the SNS leads are held to the skin of the patient using tape, sutures, etc., and the SNS electrical pulse generator is secured to the skin of the patient using tape. After proper electrode placement and appropriate analgesic efficacy have been verified (e.g., typically after a week or so of trialing), the "permanent" SNS leads and the "permanent" SNS electrical pulse generator may then be implanted internally within the torso of the patient.

Unfortunately, the current practice of using tape and/or sutures to hold the SNS leads to the skin of the patient during trialing is not completely satisfactory. By way of example but not limitation, tape and/or sutures may allow unintended movement of the SNS leads during trialing, which could displace the SNS leads from their position adjacent to the appropriate nerves in the spinal column of the patient. By way of further example but not limitation, sutures may cause additional trauma to the patient.

Therefore, a primary object of the present invention is to provide an improved method and apparatus for temporarily anchoring SNS leads to the skin of a patient during SNS trialing.

SUMMARY OF THE INVENTION

The present invention comprises the provision and use of a novel method and apparatus for temporarily anchoring SNS leads to the skin of a patient during SNS trialing. More particularly, the present invention comprises the provision and use of a novel trial lead skin fixation device for temporarily anchoring SNS leads to the skin of a patient during SNS trialing. The trial lead skin fixation device is intended to be secured to the skin of the patient, and then an SNS lead is secured to the trial lead skin fixation device, during trialing. When trialing is completed and the SNS system is to be permanently installed in the body, the trial lead skin fixation device (with the SNS lead still attached thereto) is detached from the skin of the patient and the SNS lead is pulled from the body of the patient. The "permanent" SNS leads and the "permanent" SNS electrical pulse generator may then be implanted internally within the torso of the patient.

The present invention may also be used for temporarily anchoring other elongated flexible elements to the skin of a patient.

In one form of the invention, there is provided apparatus for securing an elongated flexible element to a patient, the apparatus comprising:
a base comprising an outer face and an inner face;
an adhesive applied to the inner face of the base; and
at least one pillar upstanding from the outer face of the base.

In another form of the invention, there is provided a method for securing an elongated flexible element to a patient, the method comprising:
providing apparatus comprising:
a base comprising an outer face and an inner face;
an adhesive applied to the inner face of the base; and
at least one pillar upstanding from the outer face of the base;

securing the inner face of the base to the skin of the patient; and securing the elongated flexible element to the apparatus, wherein the step of securing the elongated flexible element to the apparatus comprises positioning the elongated flexible element alongside the at least one pillar and against the outer face of the base.

In another form of the invention, there is provided apparatus for securing an elongated flexible element to a patient, the apparatus comprising:

a base comprising an outer face and an inner face;

an adhesive applied to the inner face of the base; and a passageway formed in the outer face of the base, wherein the passageway is sized to receive the elongated flexible element.

In another form of the invention, there is provided a method for securing an elongated flexible element to a patient, the method comprising:

providing apparatus comprising:
a base comprising an outer face and an inner face;
an adhesive applied to the inner face of the base; and
a passageway formed in the outer face of the base, wherein the passageway is sized to receive the elongated flexible element;

securing the inner face of the base to the skin of the patient; and securing the elongated flexible element to the apparatus, wherein the step of securing the elongated flexible element to the apparatus comprises positioning the elongated flexible element within the passageway.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 9-14 are schematic views showing use of the trial lead skin fixation device of FIGS. 3 and 4;

FIGS. 17-26 are schematic views showing yet another trial lead skin fixation device formed in accordance with the present invention.

DETAILED DESCRIPTION OF THE PREFERRED EMBODIMENTS

Figure 1:
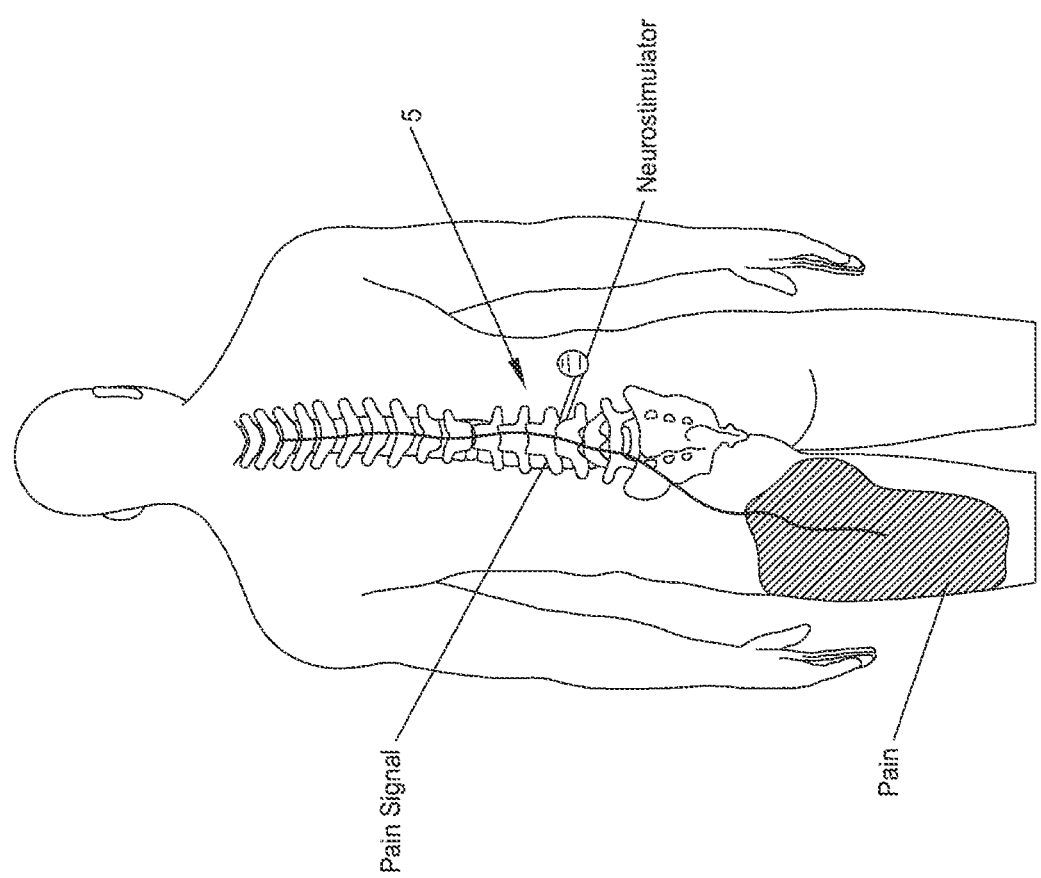
FIGS. 1 and 2 are schematic views showing an SNS system disposed in the body of a patient.
Figure 2:
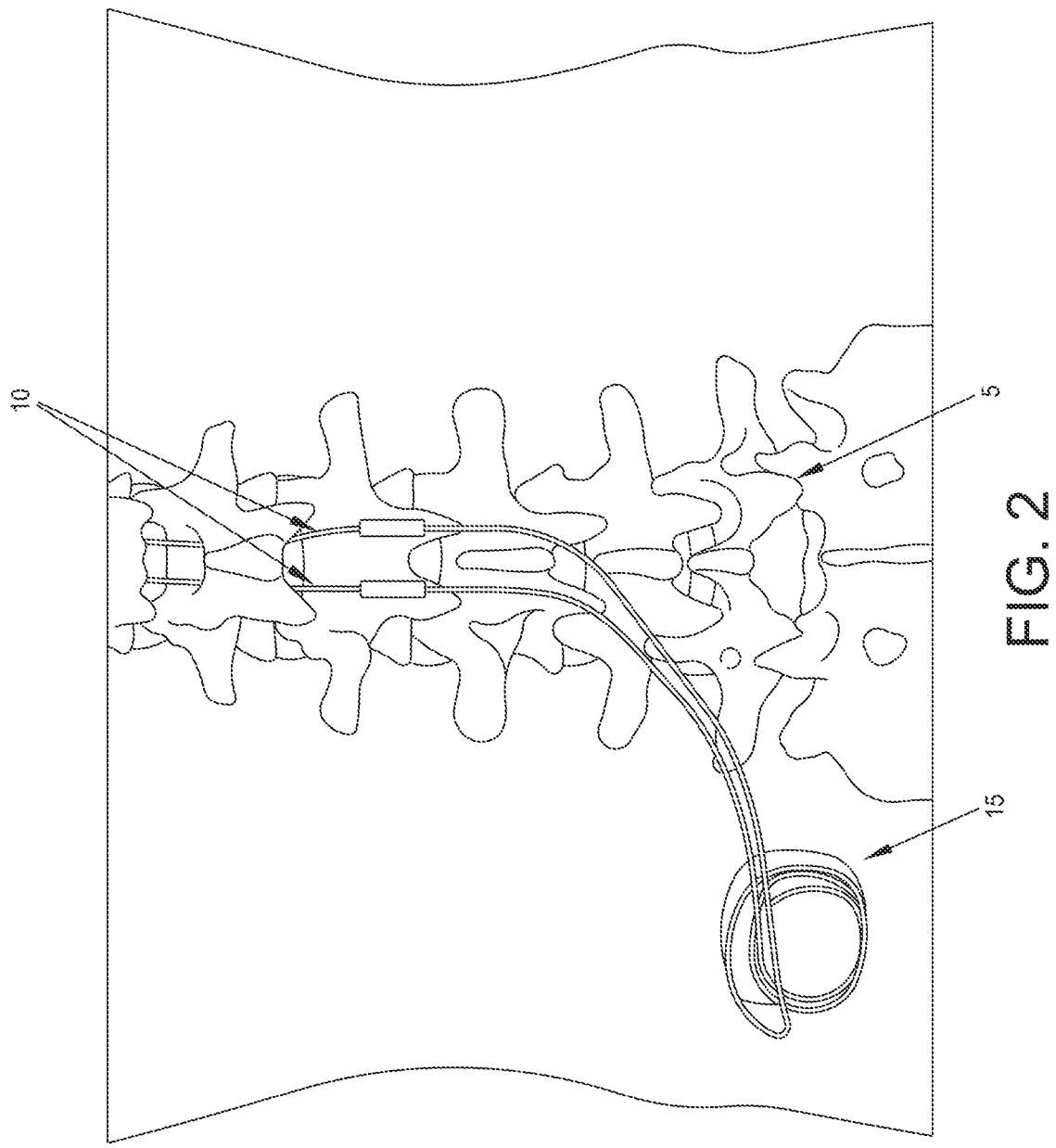
Figure 4:
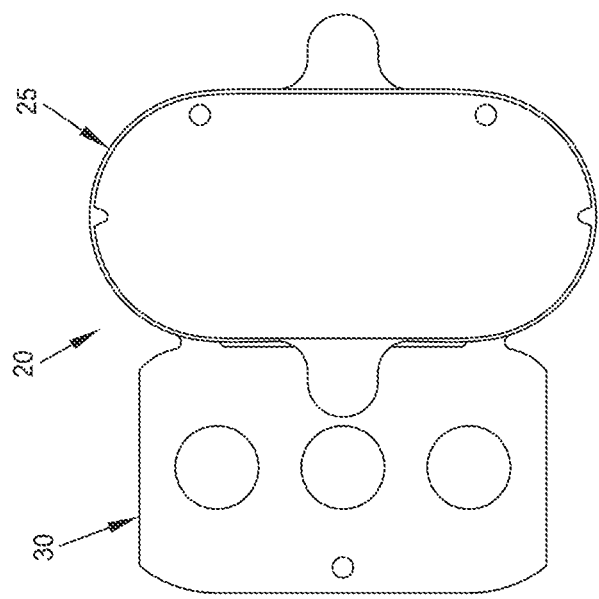
FIGS. 3 and 4 are schematic views showing the top and bottom sides, respectively, of a novel trial lead skin fixation device formed in accordance with the present invention.
Figure 3:
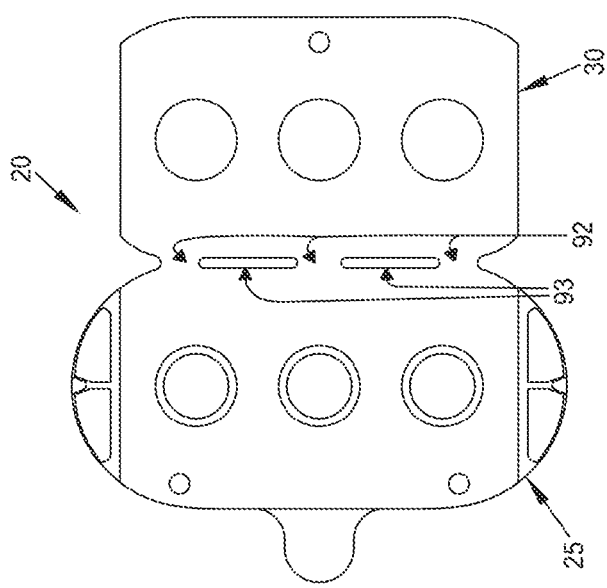
Figure 5:
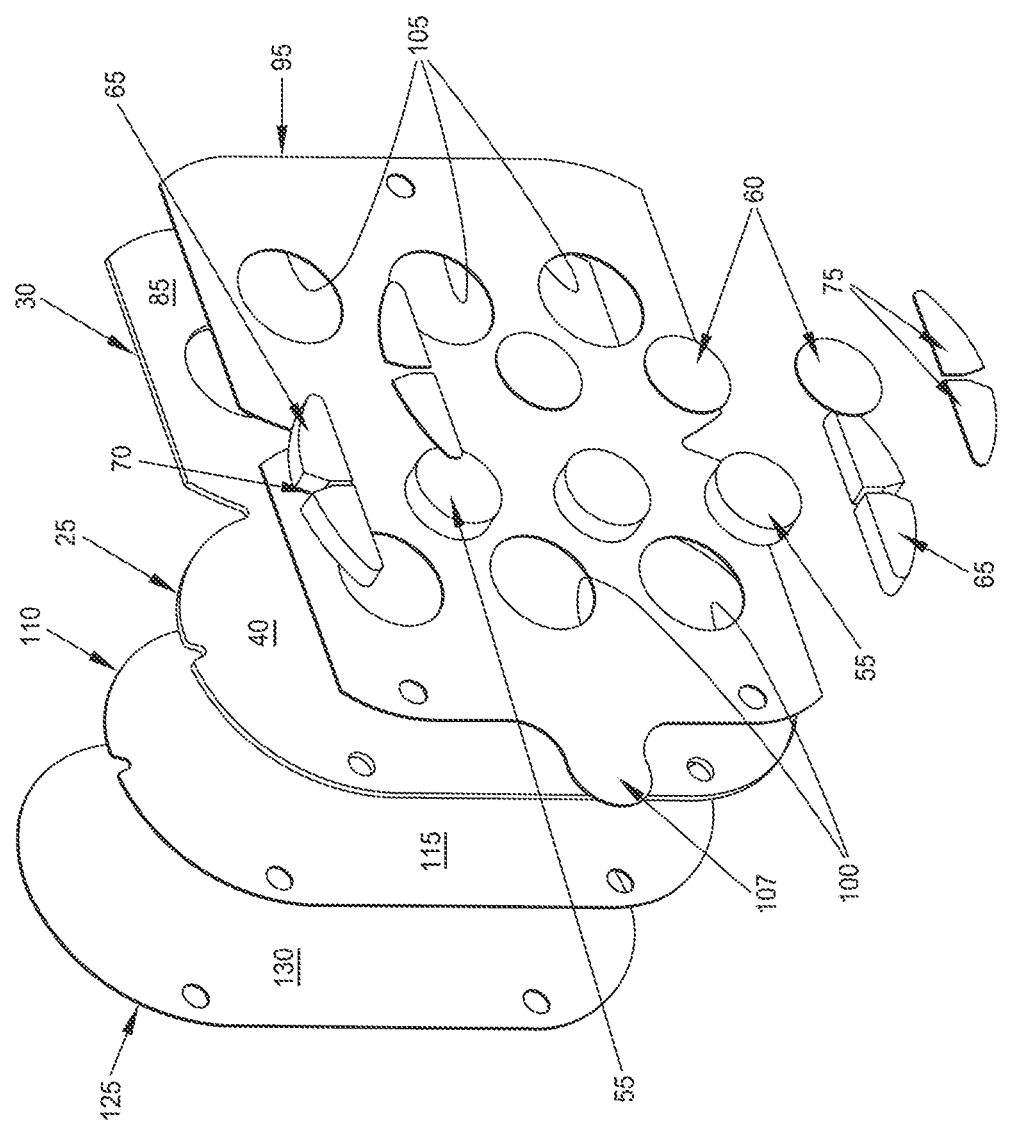
FIGS. 5 and 6 are exploded schematic views showing the top and bottom sides, respectively, of the trial lead skin fixation device of FIGS. 3 and 4.
Figure 6:
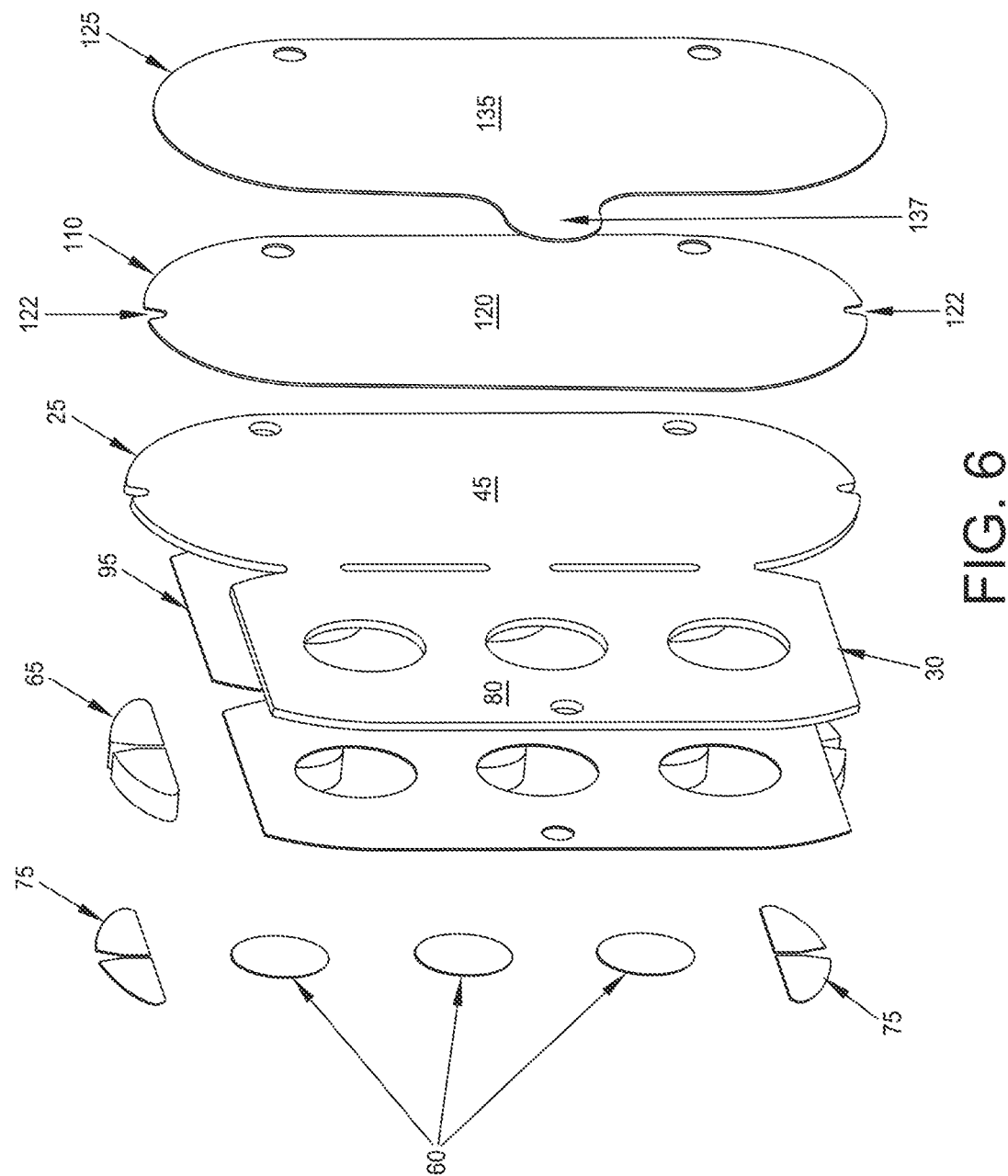
Figure 8:
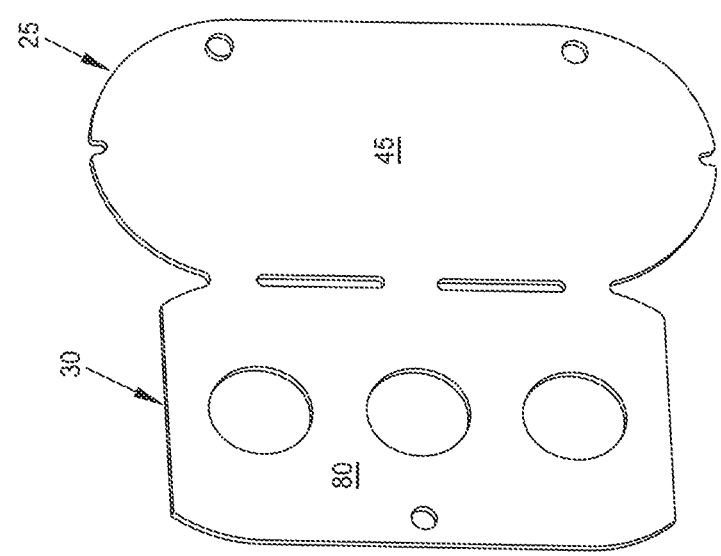
FIGS. 7 and 8 are schematic views showing the top and bottom sides, respectively, of the base and the cover of the trial lead skin fixation device of FIGS. 3 and 4.
Figure 7:
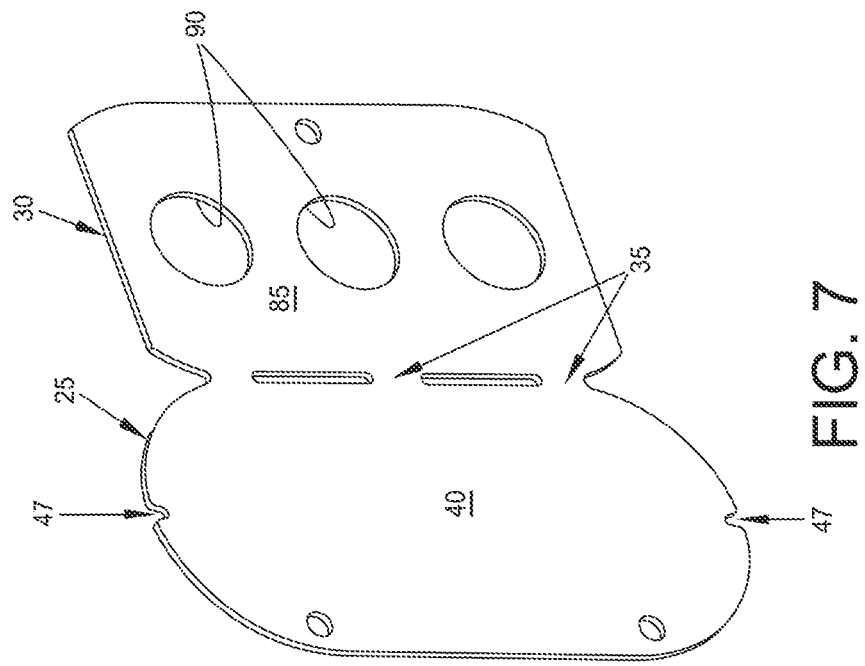

The present invention comprises the provision and use of a novel method and apparatus for temporarily anchoring SNS leads to the skin of a patient during SNS trialing. More particularly, the present invention comprises the provision and use of a novel trial lead skin fixation device for temporarily anchoring SNS leads to the skin of a patient during SNS trialing. The trial lead skin fixation device is intended to be secured to the skin of the patient, and then an SNS lead is secured to the trial lead skin fixation device, during trialing. When trialing is completed and the SNS system is to be permanently installed in the body, the trial lead skin fixation device (with the SNS lead still attached thereto) is detached from the skin of the patient and the SNS lead is pulled from the body of the patient. The "permanent" SNS leads and the "permanent" SNS electrical pulse generator may then be implanted internally within the torso of the patient.

The Novel Trial Lead Skin Fixation Device

More particularly, and looking now at FIGS. 3-8, there is shown a novel trial lead skin fixation device 20 formed in accordance with the present invention. Trial lead skin fixation device 20 generally comprises a base 25 and a cover 30. A hinge 35 movably secures cover 30 to base 25.

Base 25 has an outer (or front) face 40 and an inner (or rear) face 45. A pair of notches 47 are formed in opposing ends of base 25. A layer of adhesive (not shown in FIGS. 3-8) covers outer face 40 of base 25. A plurality of pillars (or posts) 55 are disposed on outer face 40 of base 25. Pillars 55 preferably have a height greater than the diameter of the SNS leads (or other elongated flexible elements) which are to be secured to the skin of the patient. Pillars 55 are preferably formed of a compressible foam (e.g., foam formed out of polyurethane, polyethylene, etc.). Caps 60 are disposed on the tops of pillars 55. Caps 60 are preferably formed out of a relatively stiff material, e.g., a sheet of plastic such as polyethylene terephthalate (PET). A plurality of lead-ins 65 are also disposed on outer face 40 of base 25. Lead-ins 65 are preferably also formed of a compressible foam (e.g., foam formed out of polyurethane, polyethylene, etc.). Lead-ins 65 comprise slots 70. Slots 70 in lead-ins 65 are aligned with notches 47 formed in base 25. Caps 75 are disposed on the tops of lead-ins 65. Caps 75 are preferably formed out of a relatively stiff material, e.g., a sheet of plastic such as polyethylene terephthalate (PET). Note that caps 75 do not cover slots 70 in lead-ins 65.

Cover 30 has an outer (or front) face 80 and an inner (or rear) face 85. A layer of adhesive (not shown in FIGS. 3-8) covers inner face 85 of cover 30. A plurality of holes 90 are formed in cover 30. Note that holes 90 are sized and positioned such that when cover 30 is rotated about hinge 35 so that inner face 85 of cover 30 opposes outer face 40 of base 25, pillars 55 and their caps 60 may be received in holes 90. Note also that cover 30 is sized, relative to base 25, such that cover 30 can fit between lead-ins 65 on base 25 when cover 30 is rotated about hinge 35 so that inner face 85 of cover 30 opposes outer face 40 of base 25.

Hinge 35 generally comprises flexible elements 92 extending between base 25 and cover 30. In one preferred form of the present invention, trial lead skin fixation device 20 comprises three flexible elements 92 separated by a pair of slots 93.

Base 25, cover 30 and hinge 35 are preferably formed out of a single sheet of material which is firm enough to enable base 25 and cover 30 to behave like stiff panels but flexible enough to allow elements 92 of hinge 35 to flex. In one preferred form of the invention, base 25, cover 30 and hinge 35 are formed out of an ethylene-vinyl acetate (EVA) foam material.

A release liner 95 is disposed over outer (or front) face 40 of base 25 and inner (or rear) face 85 of cover 30. Release liner 95 comprises holes 100 aligned with pillars 55 of base 25 and holes 105 aligned with holes 90 in cover 30. Note that release liner 95 is sized, relative to base 25, such that the release liner can fit between lead-ins 65 when the release liner is secured to base 25 and cover 30. Release liner 95 also comprises a "pull tab" 107.

An adhesive layer 110 is secured to inner face 45 of base 25. More particularly, adhesive layer 110 is preferably in the form of an adhesive sheet which comprises an outer (or front) face 115 and an inner (or rear) face 120. Adhesive layer 110 has its outer face 115 secured to inner face 45 of base 25. A pair of notches 122 are formed in opposing ends of adhesive layer 110. Notches 122 in adhesive layer 110 are aligned with notches 47 of base 25. Adhesive layer 110 comprises an aggressive, pressure-sensitive adhesive adapted to adhere to the skin of a patient and to stay adhered to the skin of the patient for the full length of the trialing period, e.g., approximately one week.

A release liner 125 is mounted to inner face 120 of adhesive layer 110. More particularly, release liner 125 comprises an outer (or front) face 130 and an inner (or rear) face 135. Outer face 130 of release liner 125 is secured to inner face 120 of adhesive layer 110. Release liner 125 comprises a "pull tab" 137.

Use of the Novel Trial Lead Skin Fixation Device

In use, after a spinal needle has been used to advance an SNS lead through the skin of the patient and down to the appropriate nerve in the spinal column of the patient, novel trial lead skin fixation device 20 may be used to anchor that SNS lead to the skin of the patient during trialing.

Figure 10:
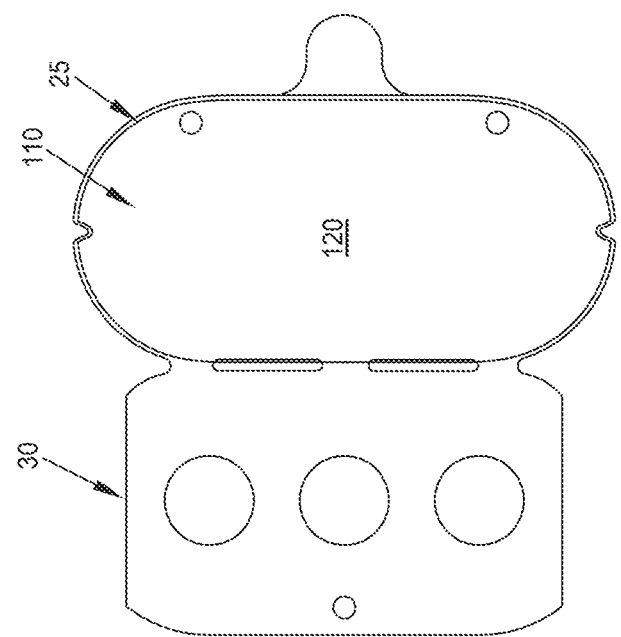
Figure 9:
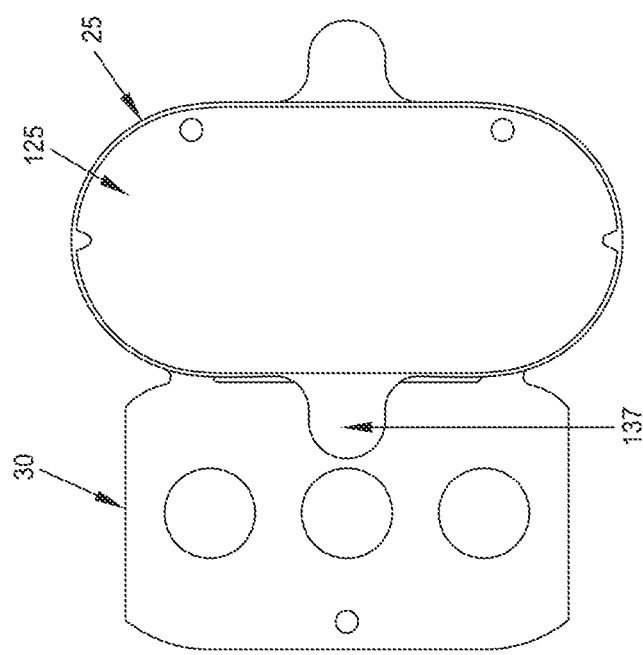
Figure 12:
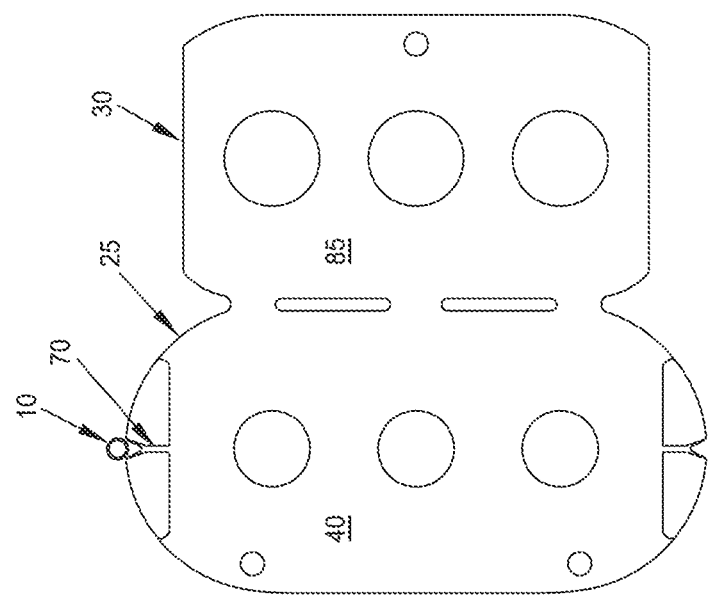
Figure 11:
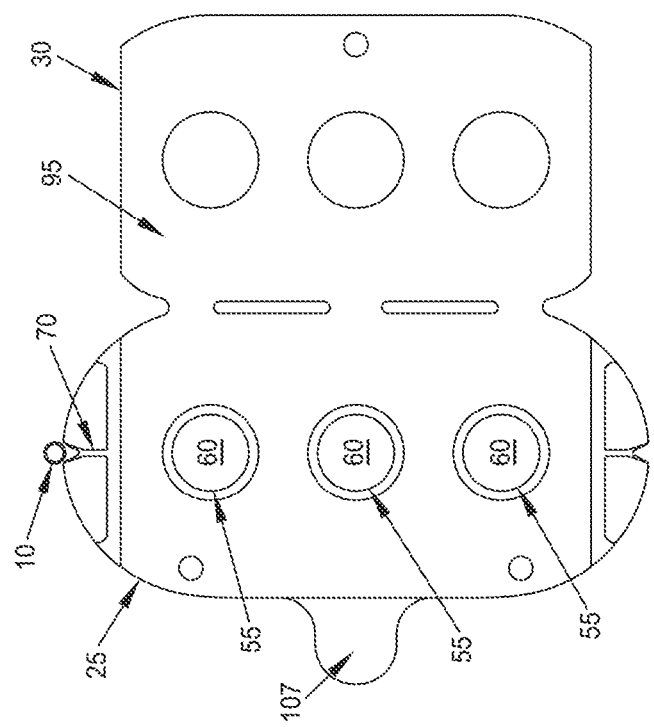

More particularly, when a trial lead skin fixation device 20 is to be used to anchor an SNS lead to the skin of a patient, release liner 125 is first removed (e.g., using pull tab 137) from inner face 120 of adhesive layer 110 (FIGS. 9 and 10). Then trial lead skin fixation device 20 is secured to the skin of the patient so that an SNS lead 10 emerging from the skin of the patient is disposed in one of a pair of aligned notches 47, 122 and adjacent to a lead-in 65. Next, release liner 95 is removed (e.g., using pull tab 107) from outer face 40 of base 25 and inner face 85 of cover 30 (FIGS. 11 and 12). Then the SNS lead is drawn through slot 70 of a lead-in 65, woven in a "serpentine" manner around pillars 55, and then out through slot 70 of the other lead-in 65. This is preferably done while the SNS lead is held under a light tension so that pillars 55 compress radially inwardly somewhat so that the SNS lead slips under caps 60 of pillars 55. Note that slots 70 of lead-ins 65 are preferably sized slightly smaller than the diameter of the SNS lead so that the SNS lead is lightly captured within slots 70, beneath caps 75 of lead-ins 65. See FIG. 13.

Note also that the adhesive positioned on outer face 40 of base 25 of trial lead skin fixation device 20 helps hold the SNS lead to outer face 40 of base 25.

Figure 14:
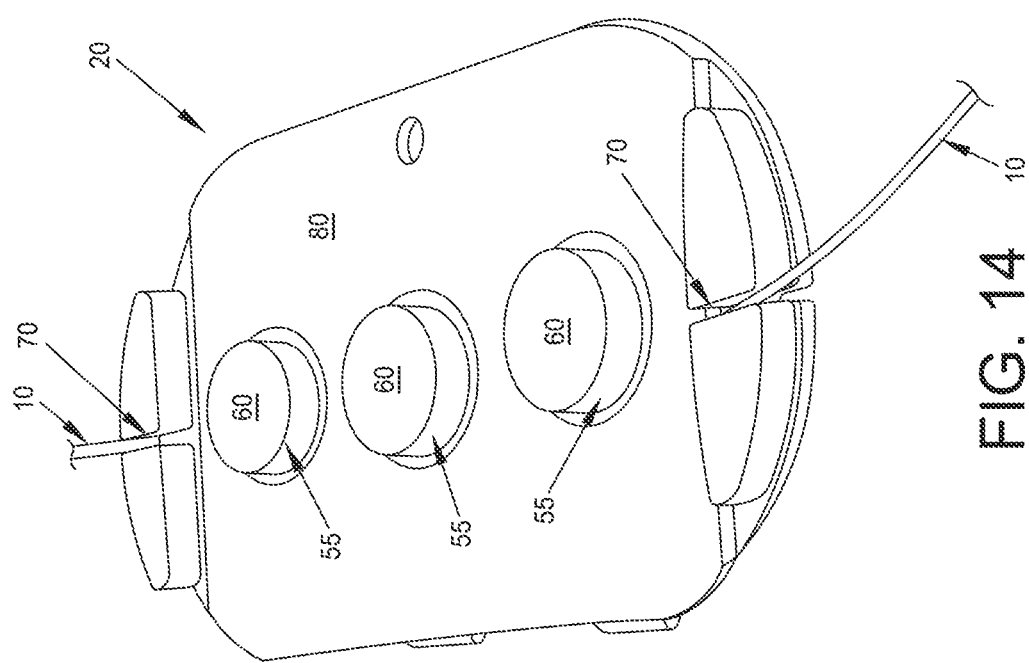

Next, cover 30 is rotated about hinge 35 so that inner face 85 of cover 30 engages outer face 40 of base 25. As this occurs, pillars 55 and their caps 60 of base 25 are received in holes 90 of cover 30, and the SNS lead is securely captured between outer face 40 of base 25 and inner face 85 of cover 30. See FIG. 14. Note that as inner face 85 of cover 30 engages outer face 40 of base 25, the adhesive on those faces helps hold cover 30 securely against base 25.

During the trialing period, the aggressive, pressure-sensitive adhesive of adhesive layer 110 keeps trial lead skin fixation device 20 securely adhered to the skin of the patient for the complete trialing period, e.g., approximately one week. Note also that during the trialing period, the SNS lead is kept securely locked in position between cover 30 and base 25, with the adhesive on inner face 85 of cover 30 and outer face 40 of base 25 keeping the cover "locked down" against the base, capturing the SNS lead therebetween.

Significantly, inasmuch as the SNS lead is woven about pillars 55 in a serpentine manner while under light tension, a capstan effect is created between the SNS lead and pillars 55. More particularly, wrapping the SNS lead around the pillars 55 with at least partial turns causes the holding forces on the SNS lead to increase exponentially due to the capstan effect. This capstan effect significantly enhances the immobilization of the SNS lead relative to pillars 55 of trial lead skin fixation device 20 (and hence enhances the immobilization of the SNS lead relative to the skin of the patient). Stated another way, the capstan forces created between the SNS lead and pillars 55 provide high holding forces which significantly enhance the capture of the SNS lead to trial lead skin fixation device 20, and hence significantly enhance capture of the SNS lead to the skin of the patient.

At the conclusion of the trialing period, trial lead skin fixation device 20 (with the SNS lead still attached thereto) is removed from the skin of the patient (note that the adhesives used to secure cover 30 to base 25 is so "sticky" that trial lead skin fixation device 20 would need to be cut open in order to release the SNS lead from the trial lead skin fixation device). Once trial lead skin fixation device 20 has been removed from the skin of the patient, the SNS lead is pulled from the body of the patient. The "permanent" SNS lead and the "permanent" SNS electrical pulse generator may then be implanted internally within the torso of the patient.

In connection with the foregoing, it will be appreciated that SNS therapy typically utilizes two SNS leads, so during trialing, two trial lead skin fixation devices 20 would typically be used, i.e., one trial lead skin fixation device 20 for each of the SNS leads. However, it should also be appreciated that, if desired, more than one trial lead skin fixation device 20 may be used for each SNS lead, e.g., such as for situations where increased "holding power" is desired.

Note that cover 30 need not be hingedly mounted to base 25. More particularly, if desired, cover 30 may be formed separately from base 25, and cover 30 may be united with base 25 by simply setting cover 30 over base 25.

Additional Novel Trial Lead Skin Fixation Devices

Figure 15:
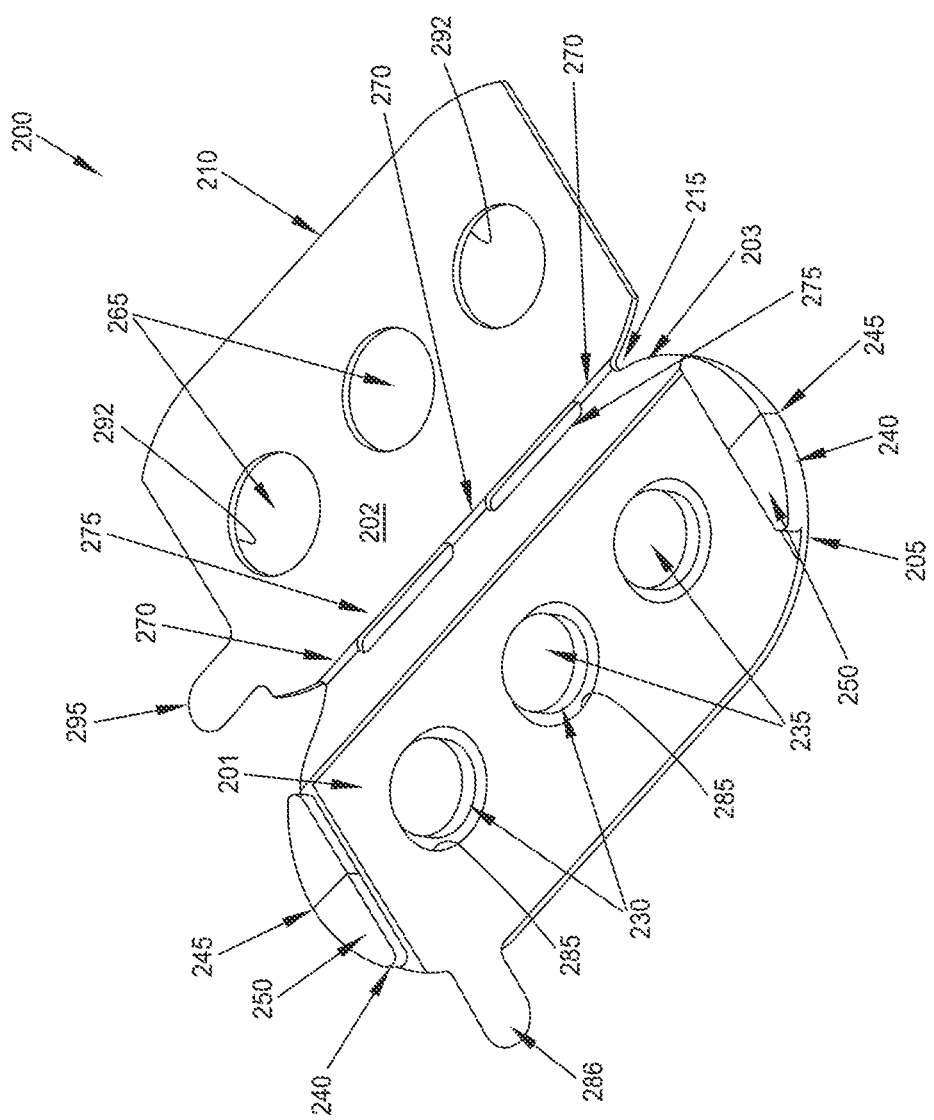
FIG. 15 is a schematic view showing another trial lead skin fixation device formed in accordance with the present invention.

Looking next at FIG. 15, there is shown another trial lead skin fixation device 200 formed in accordance with the present invention. Trial lead skin fixation device 200 is generally similar to trial lead skin fixation device 20 described above, except that release liner 95 of trial lead skin fixation device 20 is replaced by a first release liner 201 and a second release liner 202, as will hereinafter be discussed in further detail. In addition, the base of the trial lead skin fixation device has a stiffening region 203, as will also hereinafter be discussed in further detail.

More particularly, trial lead skin fixation device 200 generally comprises a base 205 and a cover 210. A hinge 215 movably secures cover 210 to base 205.

Base 205 has an outer (or front) face (not shown in FIG. 15, but analogous to outer face 40 of trial lead skin fixation device 20) and an inner (or rear) face (not shown in FIG. 15, but analogous to inner face 45 of trial lead skin fixation device 20). A pair of notches (not shown in FIG. 15, but analogous to notches 47 of trial lead skin fixation device 20) are formed in opposing ends of base 205. A layer of adhesive (not shown in FIG. 15) covers the outer face of base 205. A plurality of pillars (or posts) 230 are disposed on the outer face of base 205. Pillars 230 preferably have a height greater than the diameter of the SNS leads (or other elongated flexible elements) which are to be secured to the skin of the patient. Pillars 230 are preferably formed of a compressible foam (e.g., foam formed out of polyurethane, polyethylene, etc.). Caps 235 are disposed on the tops of pillars 230. Caps 235 are preferably formed out of a relatively stiff material, e.g., a sheet of plastic such as polyethylene terephthalate (PET). A plurality of lead-ins 240 are also disposed on the outer face of base 205. Lead-ins 240 are preferably also formed of a compressible foam (e.g., foam formed out of polyurethane, polyethylene, etc.). Lead-ins 240 comprise slots 245. Slots 245 in lead-ins 240 are aligned with the aforementioned notches formed in base 205. Caps 250 are disposed on the tops of lead-ins 240. Caps 250 are preferably formed out of a relatively stiff material, e.g., a sheet of plastic such as polyethylene terephthalate (PET). Note that caps 250 do not cover slots 245 in lead-ins 240.

Cover 210 has an outer (or front) face (not shown in FIG. 15, but analogous to outer face 85 of trial lead skin fixation device 20) and an inner (or rear) face (not shown in FIG. 15, but analogous to inner face 80 of trial lead skin fixation device 20). A layer of adhesive (not shown in FIG. 15) covers the inner face of cover 210. A plurality of holes 265 are formed in cover 210. Note that holes 265 are sized and positioned such that when cover 210 is rotated about hinge 215 so that the inner face of cover 210 opposes the outer face of base 205, pillars 230 and their caps 250 may be received in holes 265. Note also that cover 210 is sized, relative to base 205, such that cover 210 can fit between lead-ins 240 on base 205 when cover 210 is rotated about hinge 215 so that the inner face of cover 210 opposes the outer face of base 205.

Hinge 215 generally comprises flexible elements 270 extending between base 205 and cover 210. In this form of the invention, trial lead skin fixation device 200 comprises three flexible elements 270 separated by a pair of slots 275.

Base 205, cover 210 and hinge 215 are preferably formed out of a single sheet of material which is firm enough to enable base 205 and cover 210 to behave like stiff panels but flexible enough to allow elements 270 of hinge 215 to flex. In this preferred form of the invention, base 205, cover 210 and hinge 215 are formed out of an ethylene-vinyl acetate (EVA) foam material. If desired, base 205 may comprise a stiffening region 203 which has enhanced stiffness so as to facilitate bending of cover 210 about hinge 215 without causing base 205 to bend.

A first release liner 201 is disposed over the outer face of base 205. First release liner 201 comprises holes 285 aligned with pillars 230 of base 205. Note that first release liner 201 is sized, relative to base 205, such that the first release liner can fit between lead-ins 240 when the first release liner is secured to base 205. First release liner 201 also comprises a "pull tab" 286. A second release liner 202 is disposed over the inner face of cover 210. Second release liner 202 comprises holes 292 aligned with holes 265 in cover 210. Second release liner 202 comprises a "pull tab" 295.

An adhesive layer (not shown in FIG. 15, but analogous to adhesive layer 110 of trial lead skin fixation device 20) is secured to the inner face of base 205. This adhesive layer is preferably in the form of an adhesive sheet. A pair of notches (not shown in FIG. 15) are formed in opposing ends of the adhesive layer. These notches in the adhesive layer are aligned with the notches of base 205. The adhesive layer comprises an aggressive, pressure-sensitive adhesive adapted to adhere to the skin of a patient and to stay adhered to the skin of the patient for the full length of the trialing period, e.g., approximately one week.

A release liner (not shown in FIG. 15, but analogous to release liner 125 of trial lead skin fixation device 20) is mounted to the adhesive layer. The release liner comprises a "pull tab" (not shown in FIG. 15).

In use, after a spinal needle has been used to advance an SNS lead through the skin of the patient and down to the appropriate nerve in the spinal column of the patient, novel trial lead skin fixation device 200 may be used to anchor that SNS lead to the skin of the patient during trialing.

More particularly, when a trial lead skin fixation device 200 is to be used to anchor an SNS lead to the skin of a patient, the release liner is removed from the adhesive layer and trial lead skin fixation device 200 is positioned against the skin of the patient so that the SNS lead 10 emerging from the skin of the patient is disposed in a notch formed in base 205 and adjacent to a lead-in 240. Then first release liner 201 is removed (e.g., using pull tab 286) from the outer face of base 205. Then the SNS lead is drawn through slot 245 of a lead-in 240, woven in a "serpentine" manner around pillars 230, and then out through slot 245 of the other lead-in 240. This is preferably done while the SNS lead is held under a light tension so that pillars 230 compress radially inwardly somewhat so that the SNS lead slips under caps 235 of pillars 230. Note that slots 245 of lead-ins 240 are preferably sized slightly smaller than the diameter of the SNS lead so that the SNS lead is lightly captured within slots 245, beneath caps 250 of lead-ins 240.

Next, second release liner 202 is removed (e.g., using pull tab 295) from the inner face of cover 210. Cover 210 is then rotated about hinge 215 so that the inner face of cover 210 engages the outer face of base 205. As this occurs, pillars 230 and their caps 235 of base 205 are received in holes 265 of cover 210, and the SNS lead is securely captured between the outer face of base 205 and the inner face of cover 210. Note that as the inner face of cover 210 engages the outer face of base 205, the adhesive on those faces helps hold cover 210 securely against base 205.

During the trialing period, the aggressive, pressure-sensitive adhesive of the adhesive layer on the inner face of base 205 keeps trial lead skin fixation device 200 securely adhered to the skin of the patient for the complete trialing period, e.g., approximately one week. Note also that during the trialing period, the SNS lead is kept securely locked in position between cover 210 and base 205, with the adhesive on the inner face of cover 210 and the outer face of base 205 keeping the cover "locked down" against the base, capturing the SNS lead therebetween.

Significantly, inasmuch as the SNS lead is woven about pillars 230 in a serpentine manner while under light tension, a capstan effect is created between the SNS lead and pillars 230. More particularly, wrapping the SNS lead around the pillars 230 with at least partial turns causes the holding forces on the SNS lead to increase exponentially due to the capstan effect. This capstan effect significantly enhances the immobilization of the SNS lead relative to pillars 230 of trial lead skin fixation device 200 (and hence enhances the immobilization of the SNS lead relative to the skin of the patient). Stated another way, the capstan forces created between the SNS lead and pillars 230 provide high holding forces which significantly enhance the capture of the SNS lead to trial lead skin fixation device 200, and hence significantly enhance capture of the SNS lead to the skin of the patient.

At the conclusion of the trialing period, trial lead skin fixation device 200 (with the SNS lead still attached thereto) is removed from the skin of the patient (note that the adhesives used to secure cover 210 to base 205 is so "sticky" that trial lead skin fixation device 200 would need to be cut open in order to release the SNS lead from the trial lead skin fixation device). Once trial lead skin fixation device 200 has been removed from the skin of the patient, the SNS lead is pulled from the body of the patient. The "permanent" SNS lead and the "permanent" SNS electrical pulse generator may then be implanted internally within the torso of the patient.

In connection with the foregoing, it will be appreciated that SNS therapy typically utilizes two SNS leads, so during trialing, two trial lead skin fixation devices 200 would typically be used, i.e., one trial lead skin fixation device 200 for each of the SNS leads. However, it should also be appreciated that, if desired, more than one trial lead skin fixation device 200 may be used for each SNS lead, e.g., such as for situations where increased "holding power" is desired.

Note that cover 210 need not be hingedly mounted to base 205. More particularly, if desired, cover 210 may be formed separately from base 205, and cover 210 may be united with base 205 by simply setting cover 210 over base 205.

Figure 16:
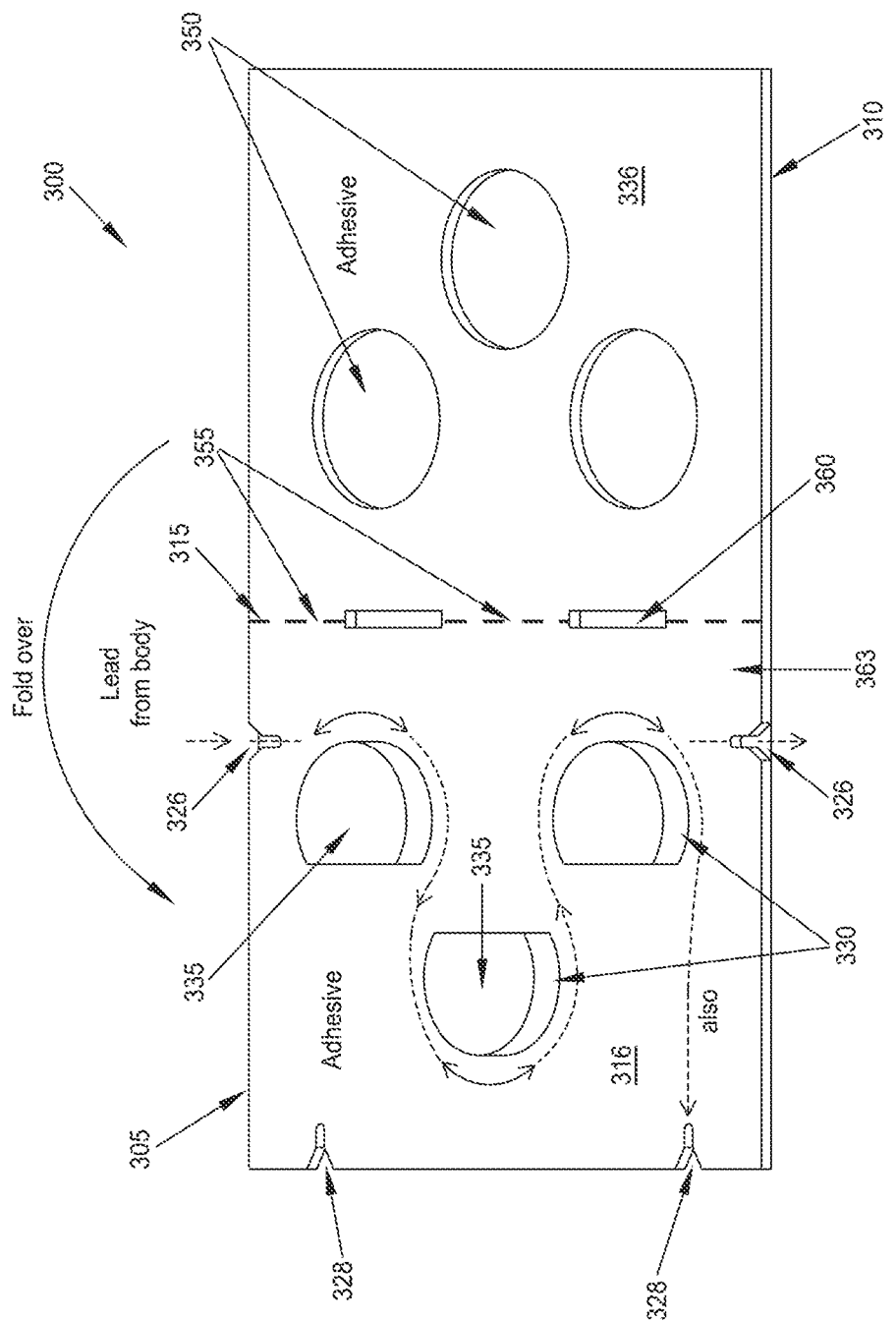
FIG. 16 is a schematic view showing still another trial lead skin fixation device formed in accordance with the present invention.

Looking next at FIG. 16, there is shown another trial lead skin fixation device 300 formed in accordance with the present invention. Trial lead skin fixation device 300 is generally similar to trial lead skin fixation device 20 described above except that lead-ins 65 (and their caps 75) of trial lead skin fixation device 25 are omitted, and except that pillars 55 (and their caps 60) of trial lead skin fixation device 20 are laterally offset from notches 47 of base 25. In addition, the base of the trial lead skin fixation device may have a stiffening region, as will also hereinafter be discussed in further detail.

More particularly, trial lead skin fixation device 300 generally comprises a base 305 and a cover 310. A hinge 315 movably secures cover 310 to base 305.

Base 305 has an outer (or front) face 316 and an inner (or rear) face (not shown in FIG. 16, but analogous to inner face 45 of trial lead skin fixation device 20). A pair of notches 326 are formed in opposing ends of base 305. Alternatively, another pair of notches 328 are formed along one edge of base 305. A layer of adhesive covers outer face 316 of base 305. A plurality of pillars (or posts) 330 are disposed on the outer face of base 305. Pillars 330 preferably have a height greater than the diameter of the SNS leads (or other elongated flexible elements) which are to be secured to the skin of the patient. Pillars 330 are preferably formed of a compressible foam (e.g., foam formed out of polyurethane, polyethylene, etc.). Caps 335 are disposed on the tops of pillars 330. Caps 335 are preferably formed out of a relatively stiff material, e.g., a sheet of plastic such as polyethylene terephthalate (PET).

Cover 310 has an outer (or front) face (not shown in FIG. 16, but analogous to outer face 85 of trial lead skin fixation device 20) and an inner (or rear) face 336. A layer of adhesive covers inner face 336 of cover 210. A plurality of holes 350 are formed in cover 310. Note that holes 350 are sized and positioned such that when cover 310 is rotated about hinge 315 so that the inner face of cover 310 opposes the outer face of base 305, pillars 330 and their caps 335 may be received in holes 350.

Hinge 315 generally comprises flexible elements 355 extending between base 305 and cover 310. In this form of the invention, trial lead skin fixation device 300 comprises three flexible elements 355 separated by a pair of slots 360.

Base 305, cover 310 and hinge 315 are preferably formed out of a single sheet of material which is firm enough to enable base 305 and cover 310 to behave like stiff panels but flexible enough to allow elements 355 of hinge 315 to flex. In this preferred form of the invention, base 305, cover 310 and hinge 315 are formed out of an ethylene-vinyl acetate (EVA) foam material. If desired, base 305 may comprise a stiffening region 363 which has enhanced stiffness so as to facilitate bending cover 310 about hinge 315 without causing base 305 to bend.

A first release liner (not shown in FIG. 16) is disposed over outer face 316 of base 305. The first release liner comprises holes aligned with pillars 330 of base 305. The first release liner may also comprises a "pull tab". A second release liner (not shown in FIG. 16) is disposed over inner face 336 of cover 310. The second release liner comprises holes aligned with holes 350 in cover 310. The second release liner may also comprises a "pull tab".

An adhesive layer (not shown in FIG. 16, but analogous to adhesive layer 110 of trial lead skin fixation device 20) is secured to the inner face of base 305. This adhesive layer is preferably in the form of an adhesive sheet. A plurality of notches (not shown in FIG. 16) are formed in the adhesive layer. These notches in the adhesive layer are aligned with notches 326, 328 of base 305. The adhesive layer comprises an aggressive, pressure-sensitive adhesive adapted to adhere to the skin of a patient and to stay adhered to the skin of the patient for the full length of the trialing period, e.g., approximately one week.

A release liner (not shown in FIG. 16, but analogous to release liner 125 of trial lead skin fixation device 20) is mounted to the adhesive layer. The release liner may also comprise a "pull tab" (not shown in FIG. 16).

In use, after a spinal needle has been used to advance an SNS lead through the skin of the patient and down to the appropriate nerve in the spinal column of the patient, novel trial lead skin fixation device 300 may be used to anchor that SNS lead to the skin of the patient during trialing.

More particularly, when a trial lead skin fixation device 300 is to be used to anchor an SNS lead to the skin of a patient, the release liner is removed from the adhesive layer and trial lead skin fixation device 300 is positioned against the skin of the patient so that the SNS lead 10 emerging from the skin of the patient is disposed in a notch formed in base 305. Then the first release liner is removed (e.g., using a pull tab) from outer face 316 of base 305. Then the SNS lead is woven in a "serpentine" manner around pillars 330. This is preferably done while the SNS lead is held under a light tension so that pillars 330 compress radially inwardly somewhat so that the SNS lead slips under caps 335 of pillars 330.

Next, the second release liner is removed (e.g., using a pull tab) from inner face 336 of cover 310. Cover 310 is then rotated about hinge 315 so that the inner face of cover 310 engages the outer face of base 305. As this occurs, pillars 330 and their caps 335 of base 305 are received in holes 350 of cover 310, and the SNS lead is securely captured between outer face 316 of base 305 and inner face 336 of cover 310.

Note that as inner face 336 of cover 310 engages outer face 316 of base 305, the adhesive on those faces helps hold cover 310 securely against base 305.

During the trialing period, the aggressive, pressure-sensitive adhesive of the adhesive layer on the inner face of base 305 keeps trial lead skin fixation device 300 securely adhered to the skin of the patient for the complete trialing period, e.g., approximately one week. Note also that during the trialing period, the SNS lead is kept securely locked in position between cover 310 and base 305, with the adhesive on the inner face of cover 310 and the outer face of base 305 keeping the cover "locked down" against the base, capturing the SNS lead therebetween.

Significantly, inasmuch as the SNS lead is woven about pillars 330 in a serpentine manner while under light tension, a capstan effect is created between the SNS lead and pillars 330. More particularly, wrapping the SNS lead around the pillars 330 with at least partial turns causes the holding forces on the SNS lead to increase exponentially due to the capstan effect. This capstan effect significantly enhances the immobilization of the SNS lead relative to pillars 330 of trial lead skin fixation device 300 (and hence enhances the immobilization of the SNS lead relative to the skin of the patient). Stated another way, the capstan forces created between the SNS lead and pillars 330 provide high holding forces which significantly enhance the capture of the SNS lead to trial lead skin fixation device 300, and hence significantly enhance capture of the SNS lead to the skin of the patient.

At the conclusion of the trialing period, trial lead skin fixation device 300 (with the SNS lead still attached thereto) is removed from the skin of the patient (note that the adhesives used to secure cover 310 to base 305 is so "sticky" that trial lead skin fixation device 300 would need to be cut open in order to release the SNS lead from the trial lead skin fixation device). Once trial lead skin fixation device 300 has been removed from the skin of the patient, the SNS lead is pulled from the body of the patient. The "permanent" SNS lead and the "permanent" SNS electrical pulse generator may then be implanted internally within the torso of the patient.

In connection with the foregoing, it will be appreciated that SNS therapy typically utilizes two SNS leads, so during trialing, two trial lead skin fixation devices 300 would typically be used, i.e., one trial lead skin fixation device 300 for each of the SNS leads. However, it should also be appreciated that, if desired, more than one trial lead skin fixation device 300 may be used for each SNS lead, e.g., such as for situations where increased "holding power" is desired.

Note that cover 310 need not be hingedly mounted to base 305. More particularly, if desired, cover 310 may be formed separately from base 305, and cover 310 may be united with base 305 by simply setting cover 310 over base 305.

Figure 17:
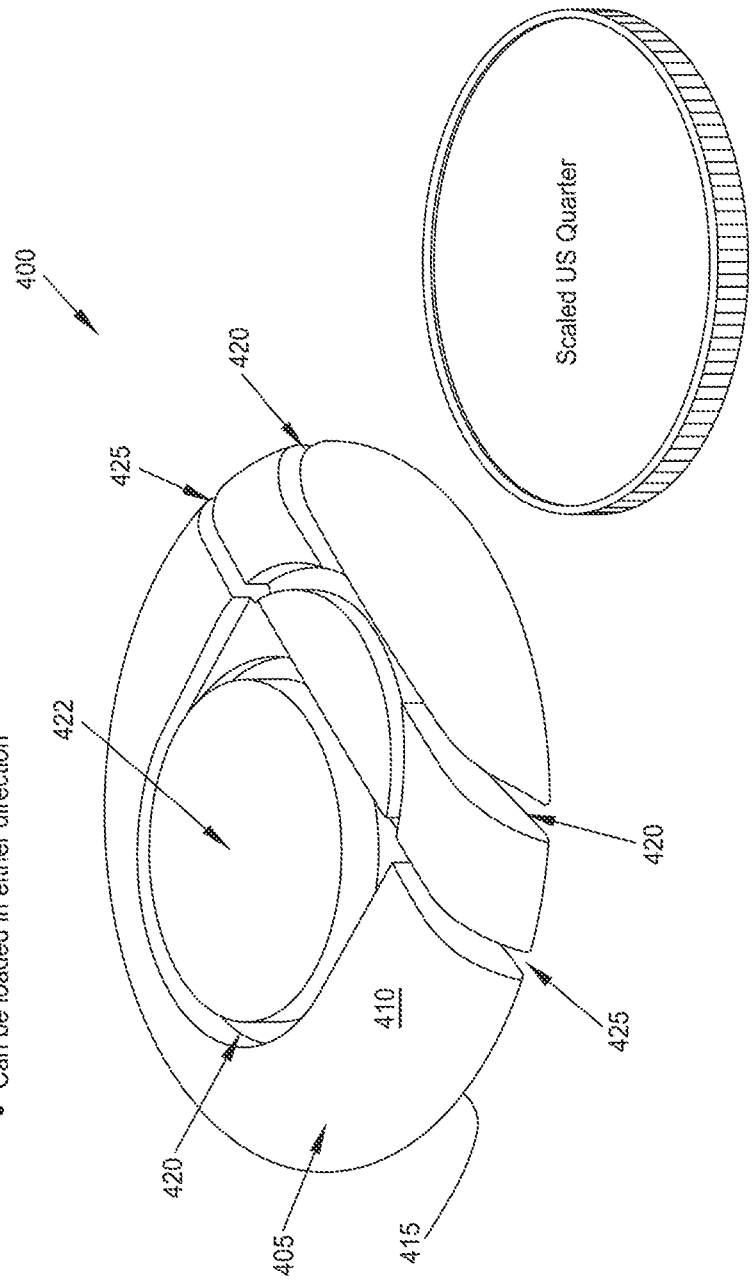

Looking next at FIGS. 17-19, there is shown yet another trial lead skin fixation device 400 formed in accordance with the present invention. Trial lead skin fixation device 400 generally comprises a base 405.

Base 405 has a top (or outer or front) surface 410 and a bottom (or inner or rear) surface 415. A series of intertwining passageways 420 are formed in top surface 410 of base 405. Passageways 420 preferably have a depth greater than the diameter of the SNS leads (or other elongated flexible elements) which are to be secured to the skin of the patient. Passageways 420 may define a pillar (or post) 422 in top surface 410 of base 405. A plurality of slots 425 are also formed in base 405. Slots 425 in base 405 intersect passageways 420 formed in base 405. In one preferred form of the invention, base 405 is formed out of a compressible material.

An adhesive layer 430 is secured to bottom surface 415 of base 405 (see FIG. 19). More particularly, adhesive layer 430 is preferably in the form of an adhesive sheet which comprises an outer (or front) face 435 and an inner (or rear) face 440. Adhesive layer 430 has its outer face 435 secured to bottom surface 415 of base 405. Adhesive layer 430 comprises an aggressive, pressure-sensitive adhesive adapted to adhere to the skin of a patient and to stay adhered to the skin of the patient for the full length of the trialing period, e.g., approximately one week.

A release liner 445 is mounted to inner face 440 of adhesive layer 430. Release liner 445 may comprise a "pull tab".

In use, and looking now at FIGS. 20-24, after a spinal needle has been used to advance an SNS lead through the skin of the patient and down to the appropriate nerve in the spinal column of the patient, novel trial lead skin fixation device 400 may be used to anchor that SNS lead to the skin of the patient during trialing.

More particularly, when a trial lead skin fixation device 400 is to be used to anchor an SNS lead to the skin of a patient, release liner 445 is first removed (e.g., using a pull tab) from inner face 440 of adhesive layer 430. Then trial lead skin fixation device 400 is secured to the skin of the patient so that an SNS lead 10 emerging from the skin of the patient is disposed in a slot 425 (see FIG. 20). Next, the SNS lead is drawn, under slight tension, through passageways 420 and then out of base 405. More particularly, and looking now at FIGS. 21-23, SNS lead 10 is slid, under slight tension, through passageways 420, wrapped around pillar 422 twice, and crossed over slot 425 (via passageway 420) and exited out of trial lead skin fixation device 400. It will be appreciated that SNS lead 10 can be tightened around pillar 422 by pulling on SNS lead 10 until there is no "slack". Note that passageways 420 and slots 425 are preferably sized slightly larger than the diameter of the SNS lead so that the SNS lead is closely received within passageways 420 and slots 425. Note also that where base 405 is formed out of a compressible material, passageways 420 and slots 425 can be sized so that base 405 can lightly grip the SNS lead received within passageways 420 and slots 425.

Significantly, inasmuch as the SNS lead is woven through passageways 420 and about pillar 422 of base 405 in a serpentine manner while under light tension, a capstan effect is created between the SNS lead and pillar 422. More particularly, wrapping the SNS lead around the pillar 422 with at least a partial turn causes the holding forces on the SNS lead to increase exponentially due to the capstan effect. This capstan effect significantly enhances the immobilization of the SNS lead relative to pillar 422 of trial lead skin fixation device 400 (and hence enhances the immobilization of the SNS lead relative to the skin of the patient). Stated another way, the capstan forces created between the SNS lead and pillar 422 provide high holding forces which significantly enhance the capture of the SNS lead to trial lead skin fixation device 400, and hence significantly enhance capture of the SNS lead to the skin of the patient.

Lastly, a bandage 465 is placed over trial lead skin fixation device 400. See FIG. 24. Bandage 465 provides additional holding power for securing trial lead skin fixation device 400 against the skin of the patient.

During the trialing period, the aggressive, pressure-sensitive adhesive of adhesive layer 430 and bandage 465 keep trial lead skin fixation device 400 securely adhered to the skin of the patient for the complete trialing period, e.g., approximately one week. Note also that during the trialing period, the SNS lead is kept securely locked in position within passageways 420, particularly due to the capstan effect created with pillar 422.

At the conclusion of the trialing period, trial lead skin fixation device 400 and bandage 465 (with the SNS lead still attached thereto) are removed from the skin of the patient. Once trial lead skin fixation device 400 has been removed from the skin of the patient, the SNS lead is pulled from the body of the patient. The "permanent" SNS lead and the "permanent" SNS electrical pulse generator may then be implanted internally within the torso of the patient.

In connection with the foregoing, it will be appreciated that SNS therapy typically utilizes two SNS leads, so during trialing, two trial lead skin fixation devices 400 would typically be used, i.e., one trial lead skin fixation device 400 for each of the SNS leads. By way of example but not limitation, two trial lead skin fixation devices 400 can be aligned side by side (see FIG. 25) and/or in a staggered configuration (see FIG. 26) on the skin of a patient. However, it should also be appreciated that, if desired, more than one trial lead skin fixation device 400 may be used for each SNS lead, e.g., such as for situations where increased "holding power" is desired.

Use of the Present Invention for Other Applications

It should be appreciated that the present invention may be used for applications other than temporarily anchoring SNS leads to the skin of a patient during SNS trialing. By way of example but not limitation, the present invention may also be used to secure other electrical leads, intravenous (IV) lines, catheters, sutures, and/or substantially any other elongated, flexible element, etc. to the skin of a patient. Significantly, by wrapping these leads, lines, catheters, sutures, and/or other elongated flexible elements at least partially around one or more curved objects (e.g., pillars, etc.), a capstan effect may be created which provides high holding forces for securing the leads, lines, catheters, sutures, and/or other elongated flexible elements to a patient.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for securing an elongated flexible element to a patient, the apparatus comprising:
    a base comprising a flat outer face and a flat inner face;
    an adhesive applied to the flat inner face of the base;
    a plurality of cylindrical pillars upstanding vertically from the flat outer face of the base, wherein each of the plurality of cylindrical pillars comprises a compressible foam material, and further wherein the plurality of cylindrical pillars are configured so that the elongated flexible element can be passed around the plurality of cylindrical pillars so as to provide a capstan effect;
    an adhesive applied to the flat outer face of the base;
    at least one lead-in upstanding from the flat outer face of the base, wherein the at least one lead-in comprises a slot for receiving the elongated flexible element;
    a cover comprising a flat outer face and a flat inner face, wherein the cover is hingedly mounted to the base by means of a living hinge; and
    an adhesive applied to the flat inner face of the cover;
    wherein the flat inner face of the cover is configured to be positioned against the flat outer face of the base after the elongated flexible element has been passed around the plurality of cylindrical pillars so as to capture the elongated flexible element between the flat inner face of the cover and the flat outer face of the base, with the adhesive of the flat inner face of the cover and the adhesive of the flat outer face of the base keeping the cover in engagement with the base.

2. Apparatus according to claim 1 wherein the elongated flexible element comprises an electrical lead.

3. Apparatus according to claim 1 wherein the elongated flexible element comprises a tube.

4. Apparatus according to claim 1 wherein the elongated flexible element comprises a suture.

5. Apparatus according to claim 1 further comprising an inner face release liner releasably covering the adhesive on the inner face of the base.

6. Apparatus according to claim 1 wherein the adhesive applied to the inner face of the base is in the form of an adhesive sheet comprising an outer face and an inner face, and further wherein the outer face of the adhesive sheet is secured to the inner face of the base.

7. Apparatus according to claim 1 wherein the base comprises at least one notch.

8. Apparatus according to claim 7 wherein the at least one notch is aligned with the centerline of the at least one pillar.

9. Apparatus according to claim 7 wherein the at least one notch is not aligned with the centerline of the at least one pillar.

10. Apparatus according to claim 7 wherein the slot of the at least one lead-in is aligned with the at least one notch of the base.

11. Apparatus according to claim 1 wherein the at least one lead-in comprises a compressible material.

12. Apparatus according to claim 11 wherein the at least one lead-in further comprises a cap, and further wherein the cap comprises a non-compressible material.

13. Apparatus according to claim 1 wherein the at least one pillar further comprises a cap, and further wherein the cap comprises a non-compressible material.

14. Apparatus according to claim 1 wherein the at least one pillar has a height greater than the diameter of the at least one elongated flexible element.

15. Apparatus according to claim 1 wherein the plurality of pillars are spaced from one another by a distance sufficient to allow the elongated flexible element to be woven around the plurality of pillars in a serpentine fashion.

16. Apparatus according to claim 15 wherein the plurality of pillars are aligned with one another.

17. Apparatus according to claim 15 wherein the plurality of pillars are laterally offset from one another.

18. Apparatus according to claim 1 wherein the cover further comprises a plurality of openings, and further wherein the plurality of openings is configured to receive the plurality of cylindrical pillars when the inner face of the cover is positioned against the outer face of the base.

19. Apparatus according to claim 1 further comprising an inner face release liner releasably covering the adhesive on the inner face of the cover.

20. Apparatus according to claim 1 further comprising an outer face release liner releasably covering the adhesive on the outer face of the base.

21. Apparatus for securing an elongated flexible element to a patient, the apparatus comprising:
- a base comprising a flat outer face and a flat inner face;
- an adhesive applied to the flat inner face of the base;
- a plurality of cylindrical pillars upstanding vertically from the flat outer face of the base, wherein each of the plurality of cylindrical pillars comprises a compressible foam material, and further wherein the plurality of cylindrical pillars are configured so that the elongated flexible element can be passed around the plurality of cylindrical pillars so as to provide a capstan effect;
- an adhesive applied to the flat outer face of the base;
- a cover comprising a flat outer face and a flat inner face, wherein the cover is hingedly mounted to the base by means of a living hinge; and
- an adhesive applied to the flat inner face of the cover;
- wherein the flat inner face of the cover is configured to be positioned against the flat outer face of the base after the elongated flexible element has been passed around the plurality of cylindrical pillars so as to capture the elongated flexible element between the flat inner face of the cover and the flat outer face of the base, with the adhesive of the flat inner face of the cover and the adhesive of the flat outer face of the base keeping the cover in engagement with the base.

* * * * *